US011133096B2

(12) United States Patent
Komatireddy et al.

(10) Patent No.: US 11,133,096 B2
(45) Date of Patent: Sep. 28, 2021

(54) METHOD FOR NON-INVASIVE MOTION TRACKING TO AUGMENT PATIENT ADMINISTERED PHYSICAL REHABILITATION

(75) Inventors: Ravi Komatireddy, San Diego, CA (US); Spencer Hutchins, San Diego, CA (US); Mitul Shah, San Diego, CA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 13/524,708

(22) Filed: Jun. 15, 2012

(65) Prior Publication Data
US 2013/0123667 A1    May 16, 2013

Related U.S. Application Data

(60) Provisional application No. 61/521,243, filed on Aug. 8, 2011.

(51) Int. Cl.
*G16H 20/30* (2018.01)
*G06T 7/20* (2017.01)
(Continued)

(52) U.S. Cl.
CPC ........... *G16H 20/30* (2018.01); *A61B 5/0002* (2013.01); *A61B 5/1114* (2013.01);
(Continued)

(58) Field of Classification Search
None
See application file for complete search history.

(56) References Cited

U.S. PATENT DOCUMENTS 5,826,578 A * 10/1998 Curchod ............. A61B 5/1121
600/595
5,980,429 A * 11/1999 Nashner ............. A61B 5/1036
434/247

(Continued)

FOREIGN PATENT DOCUMENTS

| WO | WO 2005/074372 A1 | 8/2005 |
| WO | WO 2008/099301 A1 | 8/2008 |
| WO | WO 2013/022890 A1 | 2/2013 |

OTHER PUBLICATIONS

Anderson, et al, "Lean on Wii: Physical Rehabilitation With Virtual reality and Wii Peripherals", Annual Review of Cybertherapy and Telemedicine 2010, IOS Press, 2010, ISBN: 1607505606, pp. 229-234.

(Continued)

*Primary Examiner* — Matthew Kremer
(74) *Attorney, Agent, or Firm* — Kacvinsky Daisak Bluni PLLC

(57) ABSTRACT

A system, apparatus and method are thereby provided for the non-invasive motion tracking to augment patient administered physical therapy via a motion tracking apparatus, a display, and a computing platform coupled to the motion tracking apparatus and the display. The computing platform serves to provide a menu driven interface to the patient, an instruction to the patient, a determination of the patient's motion or action in response to the instruction, a comparison between the instruction to the patient and the determination of the patient's motion or action, and to provide a feedback display to the patient. In certain embodiments, the system, apparatus and methods further includes a social networking link. In yet other embodiments, a live telemedicine link is provided, and optionally triggered based upon detection of an alert or alarm condition. In yet other embodiments, rehab tools are utilized.

4 Claims, 6 Drawing Sheets

(51) Int. Cl.
G06K 9/00 (2006.01)
A61B 5/00 (2006.01)
A61B 5/11 (2006.01)
(52) U.S. Cl.
CPC ............ *A61B 5/1128* (2013.01); *A61B 5/486* (2013.01); *A61B 5/742* (2013.01); *A61B 5/746* (2013.01); *A61B 5/7475* (2013.01); *G06K 9/00342* (2013.01); *G06T 7/20* (2013.01); *G06T 2207/30196* (2013.01)

(56) References Cited

U.S. PATENT DOCUMENTS

| | | | |
|---|---|---|---|
| 6,056,671 A * | 5/2000 | Marmer | 482/8 |
| 6,685,480 B2 | 2/2004 | Nishimoto et al. | |
| 7,308,112 B2 | 12/2007 | Fujimura et al. | |
| 7,433,024 B2 | 10/2008 | Garcia et al. | |
| 8,535,130 B2 | 9/2013 | Ciarrocchi | |
| 2001/0034014 A1* | 10/2001 | Nishimoto et al. | 434/247 |
| 2002/0135581 A1* | 9/2002 | Russell | G06T 7/0081 345/474 |
| 2004/0063480 A1* | 4/2004 | Wang | A63F 13/02 463/8 |
| 2006/0281977 A1* | 12/2006 | Soppet | 600/300 |
| 2007/0260488 A1* | 11/2007 | Heywang-Kobrunner | G16H 30/20 705/2 |
| 2008/0191864 A1* | 8/2008 | Wolfson | 340/524 |
| 2008/0267447 A1* | 10/2008 | Kelusky | G06F 19/3481 382/100 |
| 2009/0252423 A1 | 10/2009 | Zhu et al. | |
| 2009/0318775 A1* | 12/2009 | Michelson et al. | 600/301 |
| 2010/0149310 A1* | 6/2010 | Zhang et al. | 348/14.16 |
| 2010/0199228 A1 | 8/2010 | Latta et al. | |
| 2011/0054870 A1 | 3/2011 | Dariush et al. | |
| 2011/0098109 A1* | 4/2011 | Leake | A63F 13/428 463/30 |
| 2012/0296235 A1* | 11/2012 | Rupp | A61B 5/1128 600/595 |

OTHER PUBLICATIONS

Chen, et al., "Networking Telemedicine in Portable Rehabilitation Robot Monitor System", Journal of Applied Information Technology, vol. 3, No. 1, 2007, 7 pages.

Cook, "Microsoft Picks 11 Startups for new Kinect Accelerator", http://www.geekwire.com/2012/Microsoft-names-11-startups-kinect-accelarator /, Apr. 2, 2012, 6 pages.

Woodward, "Microsoft's Kinect Accelerator: The Real Scoop on the Lucky Few", http://wwwxconomy.com/seattle/2012/04/02/microsoft-kinect-accelerator-teams/ , Apr. 2, 2012, 5 pages.

Young, "Motion Sensors in Physical Therapy", Norwegian University of Science and Technology Department of Computer and Inforamation Science, Dec. 2010, 108 pages.

* cited by examiner

FIG. 3

A Web Page

Clinical Application Studio

B

Your Applications

| Image | Image |
| Image | Image |

C

Browse Therapeutic — Search
Physical Therapy | Cardiovascular | Pulmonary

Info:

Indications

Clinical Link:

D
Mail Providers/Peers
B I U abc style ▼ ≔ ≔ ○ ☐ ▦

New
Message 1:
Message 2:
Message 3:

E
◄ FEB 2008 ►
S M T W T F S
            1 2
3 4 5 6 7 8 9
10 11 12 13 14 15 16
17 18 19 20 21 22 23
24 25 26 27 28 29

Window showing details of selected date on calender

METHOD FOR NON-INVASIVE MOTION TRACKING TO AUGMENT PATIENT ADMINISTERED PHYSICAL REHABILITATION

PRIORITY CLAIM

This application claims priority to U.S. Provisional Application No. 61/521,243, filed Aug. 8, 2011, entitled "Systems. Apparatus and Methods for Non-Invasive Motion Tracking to Augment Patient Administered Physical Rehabilitation" (Ref. 921,355-026), which is incorporated herein by reference as if fully set forth herein.

FIELD OF THE INVENTION

Systems, apparatus and methods provide for monitoring the actions and position of a mammal. Particularly, they provide for the non-invasive tracking of the position and motion of a human for purposes of augmenting physical rehabilitation.

BACKGROUND OF THE INVENTION

Many acute and chronic disease states have a significant impact on the musculoskeletal system in either a direct way, e.g. primary musculoskeletal disorders; or, in an indirect way as a manifestation of musculoskeletal injury, deconditioning, or disability. From the perspective of diagnosis, a key component of the medical evaluation may include a focused evaluation of musculoskeletal performance. These include but are not limited to neurologic disorders, bone and joint disease, and injury/trauma. From the therapeutic perspective, specific, therapeutic grade musculoskeletal maneuvers are key components of treatment for musculoskeletal, neurologic, cardiovascular, and pulmonary disease states. Usually grouped under the category of "rehabilitation" therapy, or rehab for short hand terminology, which are used interchangeably herein, these maneuvers can employ techniques used by, but not limited to, physical therapists, occupational therapists, and speech pathologists to improve the overall efficacy of medical and surgical therapy by counteracting physical deconditioning, building/maintaining musculoskeletal strength, range of motion, coordination/balance, and facilitating pain relief. Example patient populations that benefit from rehab include those with primary musculoskeletal problems such as osteoarthritis, rheumatoid arthritis, disability from stroke, and patients who have undergone musculoskeletal surgery as well as patients with obesity, cardiovascular disease, and pulmonary diseases such as myocardial infarction and chronic obstructive pulmonary disease.

Rehab therapy is prescribed to patients by medical professionals and depends upon various healthcare professionals including physical therapists, occupational therapists, and physicians for care delivery. However, there are significant challenges to current models of rehab delivery and implementation. Among them are, first, traditional rehab may be cost prohibitive for both short term and long term (maintenance) use. Second, logistic difficulties may prevent patients from engaging the current outpatient rehab clinical network. Third, rehab exercises may be difficult to understand and perform correctly.

Established protocols in the form of specific musculoskeletal exercises are currently administered to patients in a variety of both outpatient and inpatient settings. These are typically initially administered via trained medical professionals (physical therapists, occupational therapists, rheumatologists, internal medicine physicians, orthopedic surgeons) during designated sessions, typically three to four weeks, with sessions typically lasting 30-60 minutes. At intermittent points throughout the rehab therapy progress, both objective and subjective measures are obtained and checked by clinic visits or visits by the relevant rehab professionals.

Outside of supervised, outpatient rehab centers, patients are encouraged to perform the appropriate rehab maneuvers at home, typically using passive instructional paper handouts that display a sequence of printed exercises. Additionally, patients may have access to digital rehab content delivered through digital media and/or downloaded from internet rehab providers that consist of animations and/or videos of rehab maneuvers.

Additionally, other motion tracking platforms in the form of commercially available accelerometer enabled or augmented motion tracking gaming systems, such as the KINECT® system from MICROSOFT®, have been used in a supervised rehab setting by allowing patients to participate in entertainment programs specific to the gaming platform.

Yet other vision based activity recognition and monitoring systems have been proposed for guided virtual rehabilitation. See, e.g. Dariusli et al. US published patent application US 2011/0054870, hereby incorporated by reference. The system follows the sequence of providing instructions for guided movement, capture of the subject's movement, tracking the movements on an Avatar, calculation of biomechanical quantities, and providing feedback to the patient.

Despite these proposed solutions, a number of serious problems remain. The inability to perform rehab exercises is a serious problem for a significant number of patients. Among the issues resulting in less than optimal rehabilitation participation and outcomes are, first, rehabilitation may become burdensome and unengaging causing treatment adherence to decline over time. Second, rehab may be is cost prohibitive. The cost of personnel, facilities, and equipment limit access to outpatient rehab services for both acute problems a well as long term maintenance therapy. Third, rehab can be time consuming. In addition to time spent on the actual exercises, there is time lost on transit to facilities and rehab appointments. These losses in turn translate to corresponding losses in productivity. Fourth, there are the challenges of exercise complexity. Rehab exercises may consist of a complex sequence of movements that could be difficult to interpret properly when presented through two dimensional, printed handouts and text descriptions, thus increasing the risk of improper therapy and injury. Fifth, there are issues of proper execution and the provision of useful feedback. Unless rehab exercises are supervised by trained clinicians, patients do not receive proper and timely feedback while executing specific maneuvers. Thus, patients may adopt improper technique for rehab exercises thereby reducing the therapeutic benefit of the exercise and possible increasing the risk of injury. Sixth, there are problems with rehab adherence. Patients prescribed outpatient rehab regimens may exhibit inconsistent patterns of compliance. This can be secondary to the factors mentioned above but can also be secondary to the perceived tedium and lack of engagement resulting in decreased adherence to the rehab exercise regimen. Seventh, tracking rehab progress can be difficult. The effectively evaluation of rehab efficacy combines both subjective patient feedback as well as objective measurements. The lack of routine, detailed measurements of patients' motion during rehab exercises, especially in the home rehab setting, makes tracking patient progress in serial rehab difficult. This is turn makes it difficult to assess the efficacy of the prescribed rehab regimen.

The systems, apparatus and methods of the present inventions seek to remedy some or all of the shortcomings of the prior systems.

BRIEF SUMMARY OF THE INVENTION

Systems, apparatus and methods combine novel automated motion tracking platform that can use a variety of video capture systems, such as cameras and other sensors to identify and track the movements of patients and clinical tools, optionally thereby enabling voice recognition, face detection and facial feature tracking for the purposes of enabling guided, medical diagnostic and therapeutic maneuvers. The system can receive and store medical-grade therapeutic, rehabilitation maneuvers that can be updated and then displayed to the patient using a computer and standard monitor such as, but not limited to, a television or computer monitor. An incorporated software platform allows for access to specially designed medical applications that include rehabilitation. The rehabilitation application can in turn allow patients to design and review a customized rehabilitation exercise routine as well as guide patients to perform specific movements consistent with established rehabilitation protocols. With real time data input from a sensor suite consisting of a motion tracking or video capture systems, such as a camera array and microphone array, the patient's motion, speech, and other patient characteristics can be accurately tracked and used by the program to provide analysis of performance both longitudinally and in comparison to a predefined motion path to provide pertinent feedback and instruction.

Optionally, specifically designed medical grade rehabilitation tools, including but not limited to, optically coded resistance bands and hand weights, can be automatically recognized by the system, such as by the video tracking system, and subsequently analyzed by the underlying software algorithm to augment the exercise sets. Specific measurements of patient motion as well as adherence can be collected and tracked to create an individualized database of performance. Further feedback and instruction can be obtained by the activation of telemedicine functionality to connect both patients and providers using the sensor platform. The system can organize and export real time performance and adherence data, as well as trends, to pertinent parties including the patient, medical providers, health care information exchanges, or third parties as appropriate to gauge efficacy, efficiency, and for entertainment value. Optionally, the use of gaming psychology and social networking tools allows improvement in adherence.

A system, apparatus and method are thereby provided for the non-invasive motion tracking to augment patient administered physical therapy via a motion tracking apparatus, a display, and a computing platform coupled to the motion tracking apparatus and the display. The computing platform serves to provide a menu driven interface to the patient, an instruction to the patient, a determination of the patient's motion or action in response to the instruction, a comparison between the instruction to the patient and the determination of the patient's motion or action, and to provide a feedback display to the patient. In certain embodiments, the system, apparatus and methods further includes a social networking link. In yet other embodiments, a live telemedicine link is provided, and optionally triggered based upon detection of an alert or alarm condition. In yet other embodiments, rehab tools are utilized.

Thus, the system provides for rehab performance tracking. Data on compliance, strength, range of motion, as well as subjective patient feedback can be recorded and sent to medical professionals to log adherence, judge therapeutic benefit, trend performance, and formulate therapeutic plans.

The system promotes economy. The system decrease both direct and indirect cost healthcare costs compared to previous solutions. The use of an automated system without constant, direct provider guidance, potentially improved rehab engagement and adherence and the potential for decreased utilization of outpatient rehab centers could lead to decreased direct costs for rehab services. Similarly, improved work productivity secondary to improved adherence and outcomes from this rehab system as well as potential reduction in prescription medication use and decreased utilization of medical imaging, outpatient, and inpatient provider services contribute to indirect cost savings.

The system provides visual guidance and real time feedback for patients with specific rehab exercise sets. In addition to providing step by step instructions for rehab exercises using an onscreen patient representation, or avatar, the system can perform a real time comparison between patient motion and intended motion consistent with the rehab exercise shown on the output display. Complex rehab sequences can be subdivided into easily understandable and manageable avatar guided instructions. The system uses this comparison to generate audio and/or visual feedback designed to instruct the patient on the proper movement. This degree of medical, therapeutic grade feedback is currently lacking in other motion tracking platforms.

The system provides convenience. An automated, guided rehab system allows patients the ability to perform rehab exercises properly, in the home or other non-clinical environment. This reduces the cost of rehab clinic utilization as well as the time needed to travel to rehab centers. Additionally, the underlying rehab software program could be accessed in a portable form factor depending on the type of monitor output used thus allowing patients flexibility in choosing the ideal location and time to engage in rehab exercises.

The system requires minimal hardware. Unlike other motion tracking technology used by commercially available gaming platforms, this implementation of motion tracking for rehab does not require, though optionally may be used with, additional hardware devices such as accelerometers, hand held controllers, or any apparatus affixed to the patient.

The system provides flexibility in a clinical environment. The form factor and usability characteristics lend the system to be used in a wide variety of clinical environments in addition to the user's place of residence. These include, but not limited to, the inpatient hospital setting, outpatient rehab clinics, skilled nursing facilities, and general outpatient medical clinics.

The system provides for training customization. In addition to being able to customize specific rehab exercise sets, as well as the look and feel of the rehab application, the user is able to customize the exercise maneuvers by using themselves by training the system for motion capture using their own body movements. The system's motion tracking algorithms can capture and store the patient's movements for various functions including for review and benchmarking as well as subsequent rehab training sessions. Thus, the user and/or patient can act as his or her own control for rehab exercises.

The system provides for extensibility. Optionally, the software platform has the ability to incorporate additional sensors for the purposes of capturing additional physiologic data while patients are engaged in the rehab routine. Example devices include but are not limited to heart rate monitors, metabolic monitoring devices, and electromyogram devices. Exemplary wireless patch based sensors are found in "Patch Based Ultrasound Sensor", U.S. application Ser. No. 13/094,678, hereby incorporated by reference in its entirety as if fully set forth herein.

The system provides for improvements in the science of rehabilitation medicine. Currently, rehabilitation medicine lacks a strong evidence based understanding of specific rehab techniques and regimens that provide the best patient outcomes. This rehab application can provide significant value by gathering the appropriate scientific evidence to test and validate rehab regimens via quantifying adherence, body movement via accurate motion tracking, and other characteristics of rehab techniques and patient usage. Thus, the rehab software application could provide a research platform for investigators to conduct research on rehab medicine.

Automated adaptation of rehab regimen based upon and longitudinal patient performance information gleaned from the patient's clinical history and performance during previous rehab regimens to dynamically update the set of exercises based on optimizing the level of difficulty for each patient.

The system provides for integration of rehab tool tracking into the motion tracking system. Rehab exercises commonly use additional therapeutic tools, or "rehab tools", such as weights and resistance bands. This system optionally uses specially coded clinical rehab tools that can be recognized by the clinical software algorithm as the patient is manipulating the tool. This recognition can be used to track appropriate rehab tool use and subsequent performance in exercises that require them. Unique features in the construction of the rehab tools allow for automatic recognition by the rehab to enable tracking of specific features such as weight resistance thus avoiding manual input of these features by patients. The coding may be an optical coding, or may comprise communicated information, such as via wireless communication using RFID or other communications systems, such as BLUETOOTH®. The rehab tools may optionally be controlled by the system, such as where the weight or resistance of a tool is changed to effect optimal rehabilitation. The system may communicate with the tools via wired or wireless communication, such as BLUETOOTH®.

Exercise sets can be changed and/or updated depending on patient engagement, performance, and or disease state. Exercise sets provided by the system are medical, therapeutic grade maneuvers that have been validated in a clinical setting as opposed to the commercial grade game software used by other motion tracing platforms.

The system provides for easy interface with other systems and apparatus through the form factor and connectivity. Options for standardized output to various types of monitors and projectors allows flexibility in use in various environments. Furthermore, the small hardware form factor allows portability and convenience. Internet connectivity also allows for potential integration of telemedicine consultation between the rehab patient and clinical rehab professionals.

The system provides for either provider directed and/or provider independence. This rehab system could be both provider directed, that is, prescribed and/or recommended by clinicians and other providers as well as initiated independently by patients when deemed appropriate.

BRIEF DESCRIPTION OF THE DRAWINGS

FIG. 3 is an exemplary image display of a clinical application studio.

DETAILED DESCRIPTION OF THE INVENTION

Figure 1:
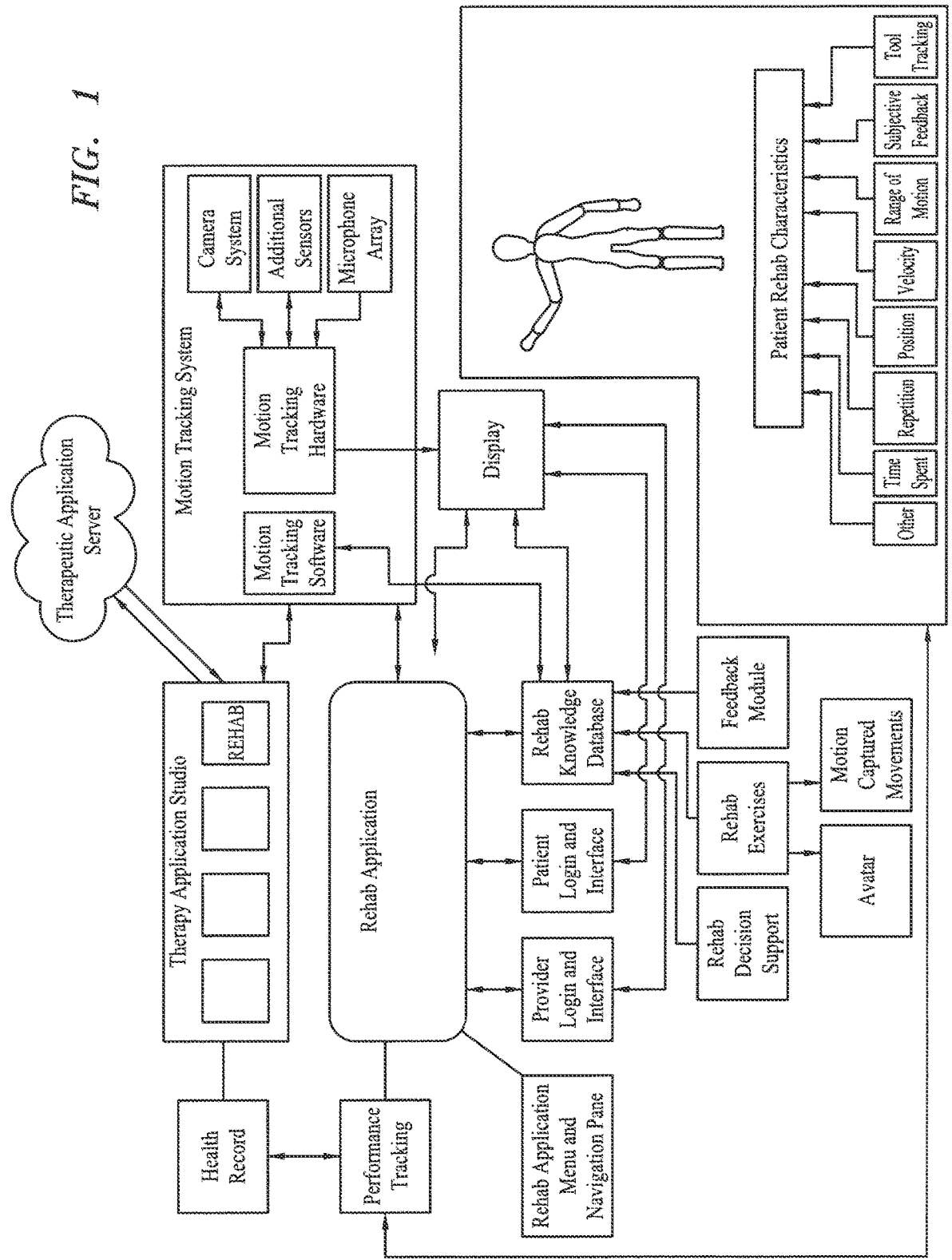
FIG. 1 is a schematic block diagram of the system and apparatus, for performing the methods herein.

FIG. 1 provides a block schematic overview of key components of the system.

Figure 2:
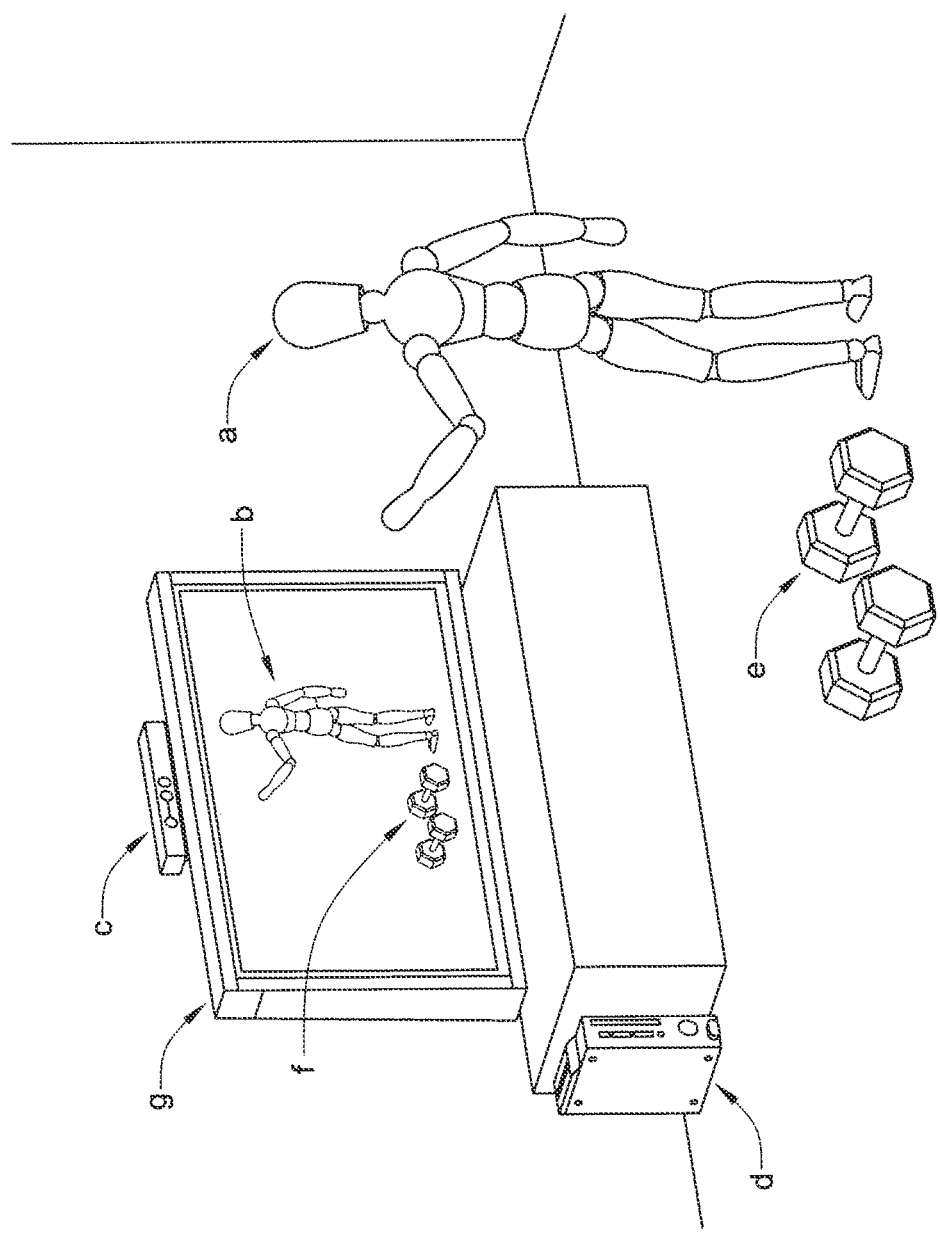
FIG. 2 is a perspective view of a therapeutic motion tracking system setup.

FIG. 2 is a perspective view of a therapeutic motion tracking system.

The motion tracking rehab system consists of several key components. The system includes a motion tracking system. Preferably, the components of the motion tracking system may include motion tracking hardware, motion tracking software, a camera system, a microphone array and additional sensors. Systems known to those skilled in the art include the KINECT® system from MICROSOFT®, the PRIMESENSE® platform, or a system of one or more cameras coupled with motion tracking software. The motion tracking apparatus may either be with or without a depth sensor. The depth sensor preferably consists of an array of cameras and structured light that is able to image and assess the environment and discreet objects within three-dimensional space within its field of view. Objects within that field of view can be assigned a depth and size that can be forwarded to software algorithms for the purposes of enabling automatic identification based upon pre-existing algorithms. In addition to measuring depth, the depth sensor is also equipped with a video camera and microphone array to enable video recording and voice/sound recognition. The patient rehab characteristics sensed may include, but are not limited to, time spent, repetition, position, velocity, range of motion, subjective feedback, and tool tracking.

A central computing platform is provided. The central computing platform hosts the clinical software platform as well as the hardware components that enable internet connectivity and connectivity to the depth sensor and external display. The central computing platform is also able to support additional add-on hardware components that could potentially be used to augment the rehab experience such as additional sensors or diagnostic tools. Components of the central computing platform may include a therapeutic application server, therapy application studio, a therapy application studio and health records. The location and interconnection of the various components described herein may be arranged in any form or manner as known to those skilled in the art, consistent with the goal of achieving the functionality of the methods describe herein.

An external display interfaces with the user/patient. A standard display in the form of a computer monitor, television, or projector can be used to view the output from the clinical software platform and the depth sensors. Optionally, a display showing three dimensional (3D) images may be utilized to provide a more realistic appearance, such as of the avatar.

A clinical software platform resides on the central computing platform and hosts the software that provides access to a suite of medical and therapeutic grade clinical applications aimed at patient care. Patients interact with the menu system using either voice navigation and/or motion gestures which can be tracked with the depth sensor. Optional interfaces include, but are not limited to, a rehab application menu and navigation pane, a provider login and interface, and a patient login and interface. Patients are presented a personalized menu where they can access pertinent clinical history and an application store where they can download and update prescribed clinical software. A rehab knowledge database interacts with a rehab decision support module, various rehab exercises, which interface with the user via an avatar and the motion capture system. The software platform maintains a connection to a centralized clinical software application server via an internet connection. Additionally, it also hosts software components necessary to enable telemedicine consultation and messaging between medical providers and patient peers.

With particular reference to FIG. 2, a patient (a) is shown using the system. Preferably, a digital representation, such as an Avatar (b) is provided of the patient (a). The avatar represents a real time static and dynamic representation of the patient. A variety of specific body and or other features of the patient are used to track patient position and motion. Any patient motion is represented on screen by a corresponding motion of the avatar. The specific patient motion can be quantified to a set of vectors that can be exported for review and used by other parts of the program. The motion tracking system allows the patient to observe his/her motion on screen in real time. Motion tracking apparatus (c) may include a depth sensor and other devices such as a camera array. It is aimed toward the patient to collect visual characteristics about the patient including position and movement it provides the information collected to the central computing platform. One possible representation of the central computing platform (d) is depicted, though any form known to those skilled in the art may be employed. The centralized computing platform may be manifested as a wide variety of hardware form factors with different interfaces, shapes and sizes. In this depiction, the hardware platform is placed in close proximity to the monitor; however, other iterations may allow for flexibility on physical location. This computing platform contains all the connectivity and computing hardware to enable the other components of motion tracking and clinical application execution. Various rehab clinical tools (e and f) may can be incorporated into the rehab system. Here a specially coded, in this case by color, rehab clinical tool to be used by the patient is recognized by the motion tracking camera platform and rehab application and placed next to the avatar in a way that corresponds to the tools position in three dimensional space. Both the type and motion of the tool can be tracked by the platform to enrich rehab therapy. All pertinent tool data including, type, motion accuracy, and adherence can be incorporated into the rehab performance tracking function of the rehab application. A display unit (g) such as an LCD television or computer monitor can be used to output information from the rehab application. Optionally, a three dimensional (3D) display may be utilized.

FIG. 3 is an exemplary image display of a clinical application studio. A user screen depicts the global therapeutic application studio where the user can access and use various motion tracking enabled applications. The various user applications (b) are displayed, or a searchable list of therapeutic or diagnostic applications obtained by the user may additionally be provided. An application browser (c) provides a searchable list of available diagnostic or therapeutic applications available from the application studio server. A health and social networking component (d) may be provided. Messaging and telemedicine link (e) to both clinical providers and social networking services provides for telemedicine consultation and support. Optionally, a schedule system (e) provides for scheduling or tracking of upcoming therapy or telemedicine sessions.

Figure 4:
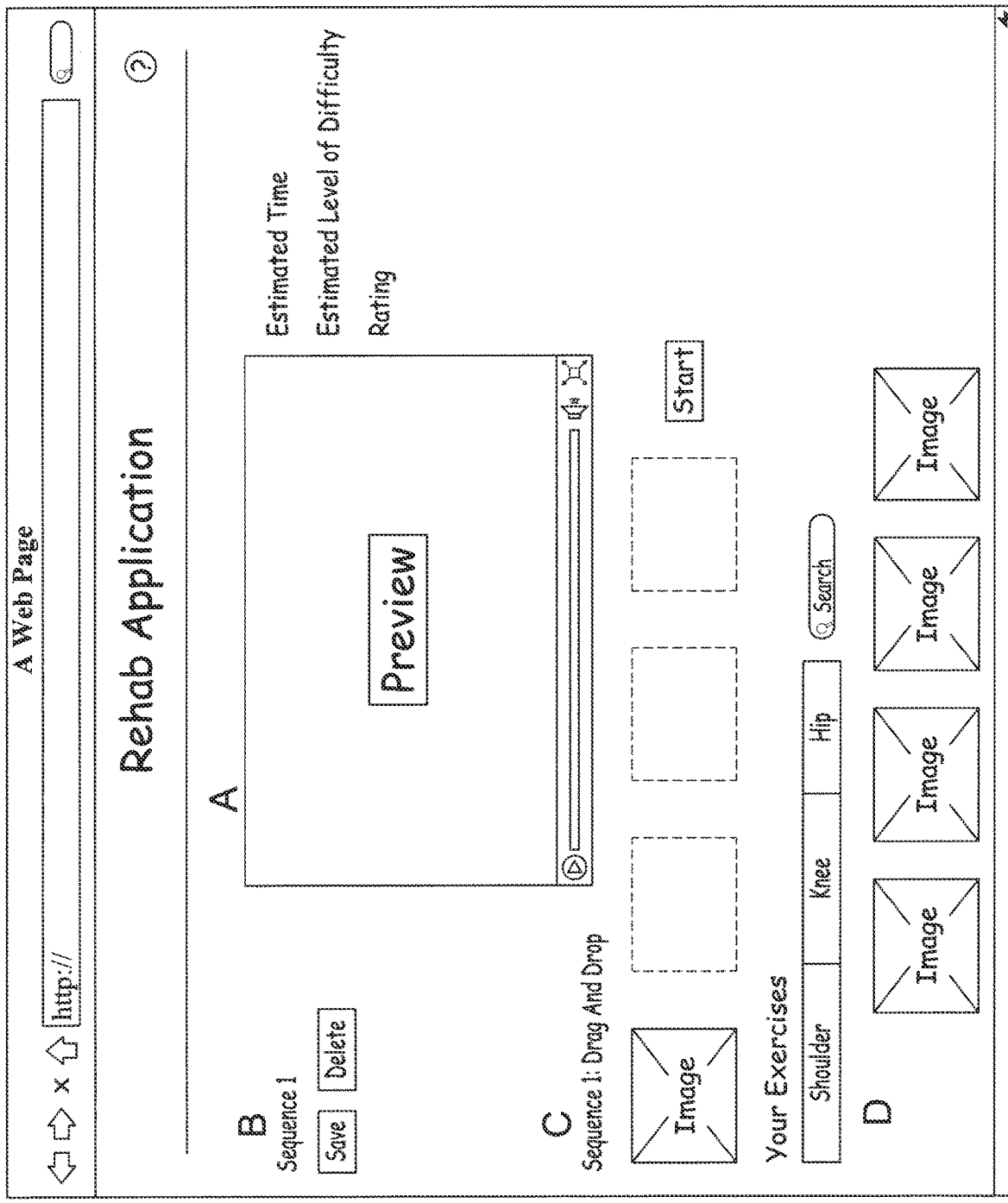
FIG. 4 is an exemplary image display of a rehab exercise selection.

FIG. 4 is an exemplary image display of a rehab exercise selection. The rehab application consists of all the components necessary to guide patients through rehab exercises. Specifically, patients who activate the rehab application from the initial software platform menu system are presented with a dashboard screen that allows them to connect via the hamlet to a central server to download rehab exercise sets, view downloaded exercise sets, select specific rehab exercises to activate, review their previous rehab exercises and performance, and export their exercise and performance records to other individuals such as their health care providers. The application serves to create a therapeutic exercise routine. Preview window (a) permits the user to preview video animations of the exercise routines in the sequence selected by the clinician or the patient. This component can also display suggested exercises, current level of difficulty, and rating. Sequence representation (c) depicts the sequence of individual exercises to create a routine. This provides the ability for user to customize the sequence of exercises from an available list and order the as appropriate. An exercise browser (d) may be provided to list the therapeutic exercises available to the user. Additional information can be obtained by selecting the individual exercises.

Upon selection of an exercise set, patients may be presented with an onscreen avatar and representation of the specific exercise. The patient has the ability to change view and change options pertaining to the specific exercise, such as level of difficulty, range of motion limits, and repetitions. Patients are able to watch instructions on how to perform the rehab exercises by the onscreen avatar. Then, they can start the rehab exercise routine by matching their body movement with the movement of the onscreen avatar. When these two movement patterns are incongruous on screen audio and visual feedback is given to the patient to correct their movement and maintain proper exercise technique. The patient can pause and resume the exercise routine at any time. Additionally, patients can completely customize their exercise routines or revert to standard exercise sets prescribed by their clinical providers.

Additionally, onscreen preprogrammed exercise routines can be changed to patient recorded routines that were captured and motion tracked while in a training environment such as an outpatient physical therapy center under the supervision of clinical providers. This functionality enables a high level of personalization and care continuity.

The onscreen avatar itself can be changed from a simple representation of the human body to a form that resembles the patient or other human in detail which also allows for customization and patient engagement. Similarly, the simulated environment of the avatar onscreen can be changed be the user according to preference.

The telemedicine link in the rehab application contains the ability to engage clinicians in the form of a telemedicine link to allow the patients' health care providers not only observe records of adherence and performance but also observe the patient perform exercises in real time to assess technique and exercise efficacy. Optionally, the system may monitor the user's vital signs and/or activities to automatically detect an alert or an alarm condition. The telemedicine link may be activated so as to connect the medical professional with the user to take corrective action to alleviate the alert or alarm condition.

Figure 5:
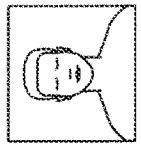
FIG. 5 is an exemplary image display of a rehab performance review and metrics screen.

FIG. 5 is an exemplary image display of a rehab performance review and metrics screen, and may include tracking and reporting features. While patients are engaged in the rehab exercises, specific variables regarding their movements are accurately measured. These include, but are not limited to, accuracy of the patient matching the presented movement, body movement velocity, position in three dimensional space, joint angle, range of motion, rotation, number of repetitions completed, system's level of accuracy in tracking the patient's movements, and time spent during each exercise. All of these metrics are logged and can be used to obtain objective measures of patient performance that can be in turn viewed by the patient and clinical providers if appropriate. The patient and/or clinical provider can access patient performance metrics to help guide therapy. Additionally, these metrics can be exported to create hard copies, health information exchanges, and online rehab or social networks. To augment the performance reports, patients and patient care givers can provide recorded audio information or text information captured by the microphone array or a connected keyboard to provide contextual annotation for future personal review or review by medical providers.

FIG. 5 shows an exemplary screen to review rehab therapy performance. Pictures and text (b) representative of the user which optionally includes detailed information about disease states and other demographic information. Timeline (c) of past, current, and future rehab sessions may be provided. Each session can be selected to provide further detail as shown. Representation (d) of user selectable rehab metrics displayed in both tabular and graphical form. Performance data may be reported in multiple formats. A clinician telemedicine link provides the user to send messages and engage in audio/visual teleconference with the patient's healthcare providers which may include orthopedic surgeons, nurses, nurse practitioners, physical therapists, and primary care physicians.

Figure 6:
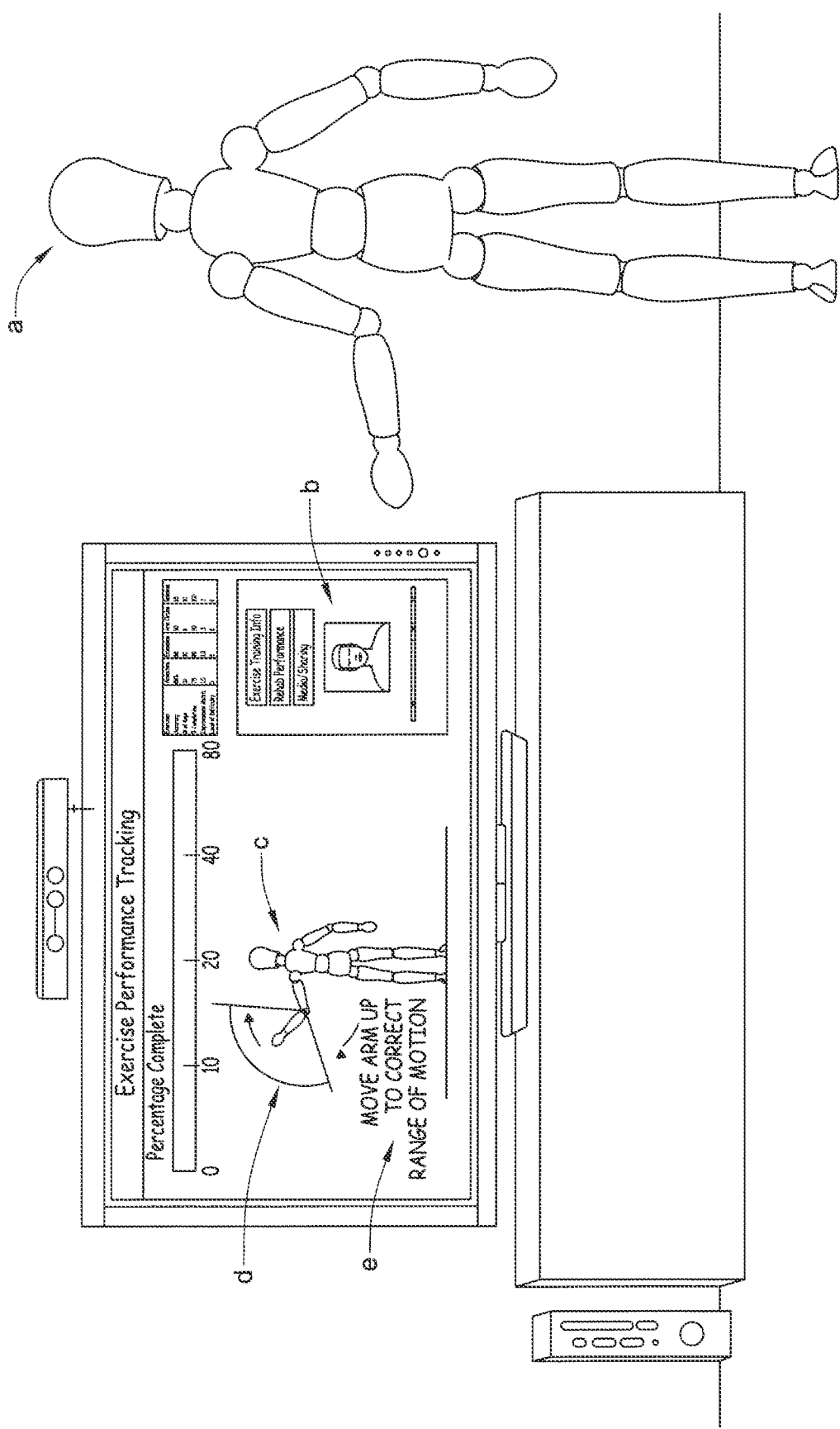
FIG. 6 is a perspective view of a display having a rehab interface with avatar guidance.

FIG. 6 shows a rehab application user interface with avatar guidance. Contextual information (b) may include, but is not limited to: patient identifying information, rehab exercise set, options, telemedicine functionality, accuracy and real time rehab performance data. It can be displayed and accessed on the monitor by the user. An avatar (c) or representation of patient/user in three-dimensional space is preferably provided. The avatar movement corresponds to patient movement using specific tracking points assigned by the motion tracking algorithm. In the case of limb movement (d), the avatar is able to instruct the user on how to move the arm using a silhouette of the user's arm and moving it in an arc. The user is instructed to match the avatar's limb movement, the corresponding user movement may be superimposed over the representation of the avatar's movement. The accuracy of the user movement matching the avatar can be obtained as well as the velocity and position of the user's limb. Real time feedback (e) may be displayed to the user. Based upon the motion of the user compared to that of the "ideal" motion derived from a predetermined rehab protocol displayed by the avatar, dynamic real time instructions may be issued by the platform to the user to ensure proper rehab exercise technique.

Additional sensors may be integrated into the system. To augment the accuracy of medical, therapeutic grade exercises and add additional insight into patient physiology, external sensors can be integrated into the performance tracking and logging feature of the rehab application and hardware platform. Example devices include additional accelerometers, motion tracking markers to assess limb rotation during clinical exercises. These devices can be added and calibrated using the rehab application and the resulting data from the additional sensors can be included in the performance reporting and on screen while the exercises are being performed.

Clinical rehab exercise tools such as dumbbells, resistance bands, and balance boards can be provided or retrofitted with motion tracking markers. Such markers may include, but are not limited to, high contrast color schemes or bar codes. These tools can be identified in terms of their characteristics (resistance level, weight) and subsequently tracked as the patient is performing the rehab exercises. The nature of rehab tool use will also be incorporated into the system's performance tracking. For the purposes of occupational therapy, the rehab tools could be expanded to include items of daily living such as eating utensils, hygiene utensils, and furniture used to train patients with neurovascular or neuromuscular disorders such as Parkinson's disease or stroke.

Various exercise sets and routines can be downloaded from a central rehab software server to their rehab application via an interact connection or portable flash memory drive. Patients can access information about these additional exercises including a brief description of their utility, peer rating, and whether they have used that set in the past.

A rehab decision support is provided. The rehab application can use algorithms, or rehab decision support, to determine whether, based upon patient performance, the level of difficulty of the exercise routine needs to be increased or decreased and can recommend alternate exercise sets to attain rehab goals.

Real time rehab social networking is optionally provided. Using the an internet connection and rehab server application the rehab software can interface with a patient selected or auto-selected peer group to compare performance results or engage in rehab exercises in a community setting.

Medical diagnostics may be performed via the system. The software platform, in addition to being able to serve therapeutic exercise sets, can also be used for diagnosis of medical disorders by presenting pathologic motions and or other physical manifestations of disease. By activating a diagnostic mode function built into the software the patient is able to exhibit specific pathology to the motion or video capture system, such as a tracking camera. Pathologic motion patterns can be recorded and analyzed by clinical decision support algorithms allowing for subsequent diagnosis to health care providers.

The central rehab server may act as a cloud based repository of therapeutic information. It may include connectivity and access to clinicians, clinical content such as therapeutic applications available for download to the central computing platform, and patient account management tools.

Additional clinical applications may be included. The rehab clinical application can be one of many medical, therapeutic grade applications downloaded or installed from the centralized therapeutic application server. Additional applications may include tools to help find rehab resources in the vicinity of the user, tools to aid in the diagnosis and management of other disease states such as cerebrovascular accident, training and therapy for occupational therapy and activities of daily living including speech training, fitness applications, and programs that use the depth sensor and motion tracking for movement disorders and sleep disorders.

All publications and patents cited in this specification are herein incorporated by reference as if each individual publication or patent application were specifically and individually indicated to be incorporated by reference. Although the foregoing invention has been described in some detail by way of illustration and example for purposes of clarity and understanding, it may be readily apparent to those of ordinary skill in the art in light of the teachings of this invention that certain changes and modifications may be made thereto without departing from the spirit or scope of the following claims.

We claim:

1. A computer-implemented method, comprising, via at least one processor of at least one computing platform:
   receiving a first set of patient body movements of a patient performing an exercise routine captured via at least one motion tracking apparatus operably coupled to the at least one processor;
   generating a patient-personalized exercise routine set based on the first set of patient body movements;
   receiving a selection of the patient-personalized exercise routine set via a menu interface presented on a display device operably coupled to the at least one processor;
   presenting an avatar on the display device presenting instructional body movements indicating instructions for performing exercises of the patient-personalized exercise routine set,
   receiving a second set of patient body movements of the patient performing the patient-personalized exercise routine set captured via the at least one motion tracking apparatus;
   determining an accuracy of the second set of patient body movements matching the instructional body movements; and
   presenting visual feedback indicating the accuracy on the display device,
   wherein the first set of patient body movements is performed under supervision of a clinical provider at an outpatient center, and the second set of patient body movements is performed at a location different from the outpatient center.

2. The method of claim 1, the avatar presented to provide the instructional body movements in mirror image to the patient.

3. The method of claim 1, the visual feedback comprising superimposing the second set of patient body movements over the instructional body movements of the avatar.

4. The method of claim 1, the processor to execute a rehabilitation program to:
   detect at least one coded rehabilitation tool, and
   present, via the display device, an image of the at least one coded rehabilitation tool next to the avatar.

* * * * *